US00PP12974P2

(12) United States Plant Patent
Bradford

(10) Patent No.: US PP12,974 P2
(45) Date of Patent: Sep. 17, 2002

(54) PEACH TREE NAMED 'ICE PRINCESS'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 26 days.

(21) Appl. No.: 09/732,081

(22) Filed: Dec. 8, 2000

(51) Int. Cl.[7] ..... A01H 5/00
(52) U.S. Cl. ..... Plt./196
(58) Field of Search ..... Plt./196

(56) References Cited

U.S. PATENT DOCUMENTS

PP7,066 P 12/1989 Bradford et al.
PP11,199 P 2/2000 Bradford et al.

*Primary Examiner*—Bruce R. Campell
*Assistant Examiner*—Susan B. McCormick

(57) ABSTRACT

The present invention relates to a peach tree, botanical classification *Prunus persica* cultivar 'ICE PRINCESS', and more particularly to a new and distinct variety broadly characterized by a large size, virgorous, hardy, self-fertile, productive and regular bearing tree. The fruit matures under the ecological conditions described approximately the first week in July, with first picking on Jun. 28, 2000. The fruit is uniformly large in size, very good in flavor, globose to oblate in shape, freestone in type, firm in texture, white in flesh color, and mostly red to pink in skin color. The variety was developed as a first generation cross using 'Diamond Princess' (U.S. Plant Pat. No. 7,066) yellow flesh peach as the selected seed parent and an unnamed white flesh peach as the selected pollen parent.

1 Drawing Sheet

BOTANICAL CLASSIFICATION

*Prunus persica* cultivar 'ICE PRINCESS'.

BACKGROUND OF THE VARIETY

In a continuing effort to improve the quality of shipping fruits, I, the inventor, typically hybridize a large number of nectarine, peach, plum, apricot, and cherry seedling each year. The present invention relates to a new and distinct variety of peach tree, which has been denominated varietally as 'ICE PRINCESS'. The present variety was hybridized by me in 1992, grown as a seedling on its own root in my greenhouse, and transplanted to a cultivated area of our experimental orchard at Bradford Farms near Le Grand, Calif. in Merced County (San Joaquin Valley). It was developed as a first generation cross using 'Diamond Princess' (U.S. Plant Pat. No. 7,066) yellow flesh peach as the selected seed parent and an unnamed white flesh peach as the selected pollen parent. Subsequent to origination of the present variety of peach tree, I asexually reproduced it by budding and grafting in the experimental orchard described above, and such reproduction of plant and fruit characteristics were true to the original plant in all respects. The repoduction of the variety included the use of 'Nemaguard' rootstock (unpatented) upon which the present variety was compatible and true to type.

The present variety is similar to its selected seed parent, 'Diamond Princess' (U.S. Plant Pat. No. 7,066) peach, by producing freestone peaches that are globose to oblate in shape, firm in texture, and mostly red in skin color, but is distinguished therefrom and an improvement thereon by producing fruit that is white instead of yellow in flesh color, that is subacid instead of acid in flavor, that is somewhat larger in size, and that matures about 8 days earlier.

The present variety is most similar to 'Coral Princess' (U.S. Plant Pat. No. 11,199) peach by producing peaches that are white with virtually no red bleeding in flesh color, subacid and sweet in flavor, mostly red in skin color, and ripen approximately the first week in July, but is distinguished therefrom and an improvement thereon by blooming about seven days earlier and by producing fruit that is larger in size and that is freestone instead of clingstone in type, yet has a stone cavity with virtually no surrounding hollow space.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 1, 2000 on the original tree during its seventh growing season. All major color code designations are by reference to the Inter-Society Color Council, National Bureau of Standards. Common color names are also used occasionally.

TREE

Size: Large, reaching and maintaining a height of 13' [3.96 m.] and a spread of 9' [2.74 m.] after seven growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.
Production: Very productive, thinning necessary.

Fertility: Self-fertile.
Bearing: Regular bearer with no alternate bearing yet observed.
Trunk:
*Size*.—Medium, reaching a maximum diameter of 5.5" [140 mm.] after the seventh growing season.
*Texture*.—Rough.
*Bark color*.—Brownish gray [64. brGr].
*Lenticels*.—Numerous. Color: Strong orange yellow [68. s.OY]. Typical Size: ¼" to ½" [6.4–12.7 mm.].
Branches:
*Size*.—Diameter of scaffold is 3" [76 mm.] measured 12" above the crotch, typical of *Prunus persica,* and dependent upon cultural practices and climatic conditions.
*Texture*.—Smooth on 1st year wood, increasing roughness with age.
*Color*.—1st Year Wood Topside: Grayish red [19. gy.R]. 1st Year Wood Underside: Brilliant yellow green [116. brill.YG]. Older Wood: Moderate brown [58. m.Br].
*Lenticels*.—Numerous. Color: Moderate orange yellow [71. m.OY]. Typical Size: 1/16" to ¼" [1.6–6.4 mm.].
Leaves
*Size*.—Large. Average Length: 6.5" [165 mm.]. Average Width: 1 7/16" [36.5 mm.].
*Arrangement*.—Alternate.
*Thickness*.—Medium.
*Form*.—Elliptical.
*Apex*.—Acuminate.
*Base*.—Acute.
*Surface*.—Smooth.
*Color*.—Dorsal Surface: Dark olive green [126. d.OlG]. Ventral Surface: Moderate olive green [125. m.OlG].
*Margin*.—Finely serrate.
*Venation*.—Pinnately net veined.
*Petiole*.—Average Length: ½" [12.7 mm.]. Average Thickness: ⅙" [1.6 mm.]. Color: Light yellow green [119. l.YG].
*Stipules*.—Numerous, 2 per leaf, up to 6 per growing tip. Average Length: ⅜" [9.5 mm.].
*Glands*.—Numbers: 2 to 6. Position: Alternately positioned on the petiole and base of blade. Size: Medium. Form: Reinform. Color: Light yellow green [119. l.YG].
*Leaf buds*.—Pointed.
Flower buds:
*Hardiness*.—Hardy, with respect to central California winters.
*Diameter*.—Typically ⅜" [9.5 mm.] 1 week before bloom.
*Length*.—Typically ¾" [19.1 mm.] 1 week before bloom.
*Form*.—Conic, not appressed.
*Surface*.—Pubescent.
*Color*.—Moderate purplish red [258. m.pR].
Flowers: Perfect, complete, perigynous, usually a single pistil, typically thirty or more stamens, five sepals and petal locations alternately positioned.
*Type*.—Showy.
*Average flower diameter*.—1⅞" [47.6 mm.].
*Number of petals*.—Usually five, very few doubles.
*Petal shape*.—Circular.
*Petal margin*.—Slightly wavy.
*Average petal diameter*.—¾" [19.1 mm.].
*Petal color*.—Pale purplish pink [252. p.pPk].
*Anther color*.—Dark red [16. d.R] when first open.
*Stigma color*.—Moderate yellow [87. m.Y].
*Sepal color*.—Dark purplish red [259. d.pR].
*Sepal length*.—3/16" [4.8 mm.].
*Sepal width*.—3/16" [4.8 mm.].
*Average pistil length*.—¾" [19.1 mm.].
*Average stamen length*.—11/16" [17.5 mm.].
*Fragrance*.—Moderate when nectar is present.
*Blooming period*.—Early compared with other varieties.
*Onset of bloom*.—One percent on Feb. 21, 2000.
*Duration of bloom*.—One to two weeks, dependent on ambient temperature.

FRUIT

Maturity when described: Hard ripe, Jul. 1, 2000.
Date of first picking: Jun. 28, 2000.
Date of last picking: Jul. 10, 2000.
Size: Uniform, large.
*Average diameter axially*.—2 15/16" [74.6 mm.].
*Average diameter across suture plane*.—3⅛" [79.4 mm.].
*Typical weight*.—8.5 ounces [241 grams].
Form: Uniform, symmetrical, globose to oblate.
*Longitudinal section form*.—Elliptical, compressed axially.
*Transverse section through diameter*.—Round.
Suture: A sharp groove in the stem cavity becoming a shallow groove and extending from the base to the apex with a marked depression just beyond the pistil point.
Ventral surface: Rounded, lipped stronger toward the apex.
Lips: Unequal.
Cavity: Flaring, elongated in the suture plane, suture showing on both sides, Pale yellow [98. p.Y] stem markings typical.
*Depth*.—½" [12.7 mm.].
*Breadth*.—⅞" [22.2 mm.].
Base: Somewhat cuneate to truncate.
Apex: Rounded to truncate.
Pistil point: Apical, negligible in length, depressed with the suture.
Stem: Medium.
*Average length*.—⅜" [9.5 mm.].
*Average width*.—3/16" [4.8 mm.].
Skin:
*Thickness*.—Medium.
*Texture*.—Medium.
*Tenacity*.—Tenacious to flesh.
*Astringency*.—Slight to none.
*Tendency to crack*.—None observed.
*Color*.—Dark red [16. d.R] over a Moderate pink [5. m.Pk] background with some Pale yellow [89. p.Y] freckling toward the apex.
Down: Moderate, short, does not roll up when rubbed.
Flesh:
*Color*.—Yellowish white [92. yWhite] from the skin to the stone with the slightest amount of Moderate red [15. m.R] streaking very close to the stone.
*Surface of pit cavity*.—Yellowish white [92. yWhite] to Pale pink [7. p.Pk] fibers cleanly detaching from the tightly surrounded stone.
*Amygdalin*.—Scarce.
*Juice*.—Moderate, rich.
*Texture*.—Firm, crisp.
*Fibers*.—Abundant, fine.

*Ripens*.—Slightly earliest toward the apex.
*Flavor*.—Subacidic and sweet, ranging from 14 to 18 brix.
*Aroma*.—Slight.
*Eating quality*.—Very good.

STONE

Type: Freestone.
Form: Oval.
Base: Straight.
Apex: Acute.
Sides: Equal.
Surface: Irregularly furrowed near the apex and pitted toward the base.
Ridges: Jagged toward the base.
Color: Light brown [57. l.Br].
Average pit wall thickness: ¼" – [6.4 mm.].
Average width: 15⁄16 [23.8 mm.].
Average length: 1⅛" [28.6 mm.].
Tendency to split: None observed.
Kernel:
*Form*.—Oval.
*Color*.—Pale yellow [89. p.Y] with Moderate brown [58. m.Br] veins when first exposed.
*Taste*.—Bitter.
*Viable*.—Yes.
*Average width*.—½" [12.7 mm.].
*Average length*.—¾" [19.1 mm.].
Pellicle color: Moderate brown [58. m.Br].
Amygdalin: Abundant.

USE

Market: Fresh and long distance shipping.
Keeping quality: Fruit quality observed to remain in good condition is excess of 20 days in standard cold room at 36° Fahrenheit [2° Celsius].
Resistance to insects: No unusual susceptibilities noted.
Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that most similar to 'Coral Princess' (U.S. Plant Pat. No. 11,199) peach by producing peaches that are white with virtually no red bleeding in flesh color, subacid and sweet in flavor, mostly red in skin color, and ripen approximately the first week in July, but is distinguished therefrom and an improvement thereon by blooming about seven days earlier and by producing fruit that is larger in size and that is freestone instead of clingstone in type, yet has a stone cavity with virtually no surrounding hollow space.

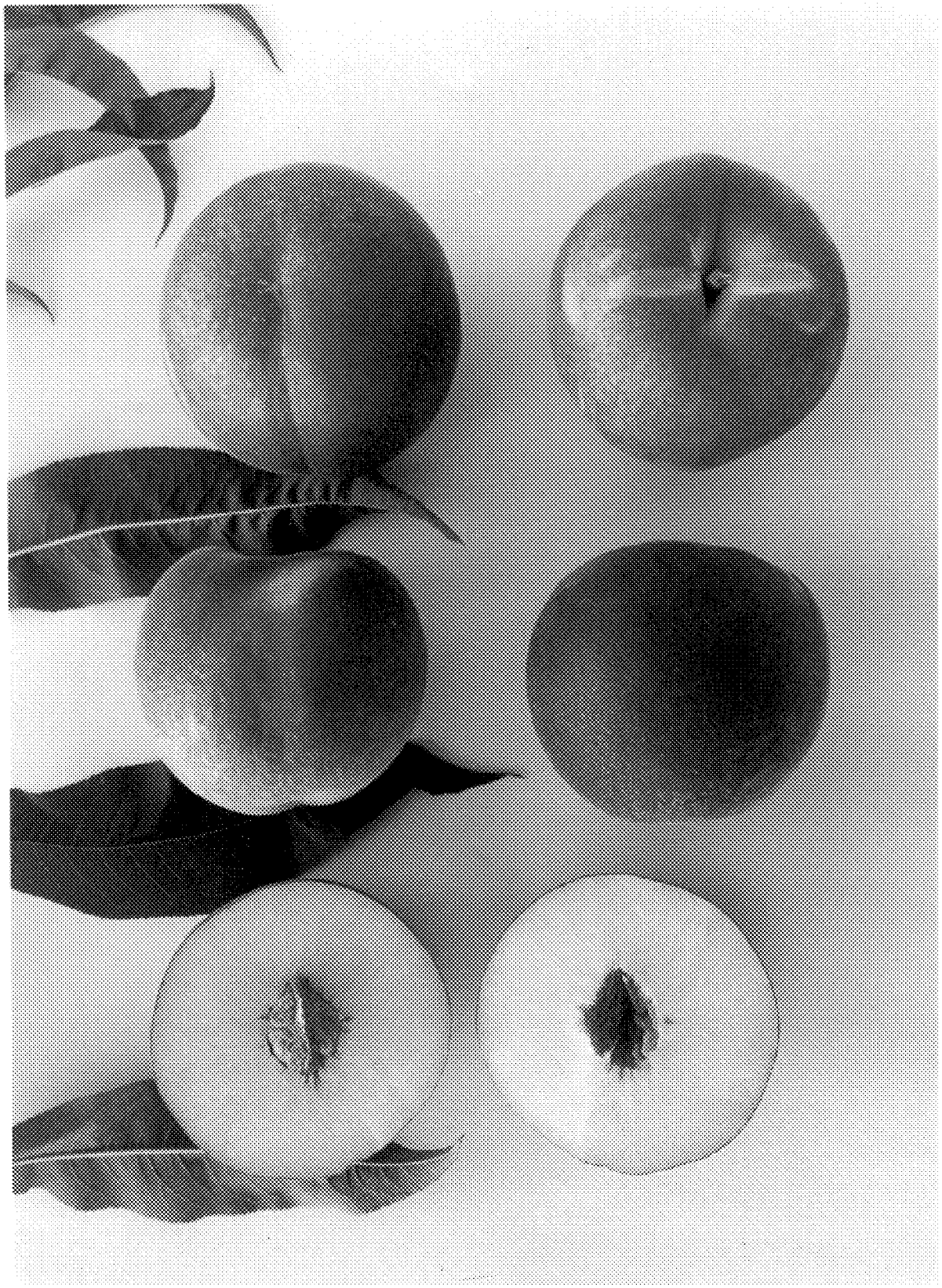

* * * * *